(12) United States Patent
Mimura

(10) Patent No.: US 7,631,971 B2
(45) Date of Patent: Dec. 15, 2009

(54) OPHTHALMIC APPARATUS

(75) Inventor: Yoshiaki Mimura, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 384 days.

(21) Appl. No.: 11/631,158

(22) PCT Filed: Aug. 22, 2005

(86) PCT No.: PCT/JP2005/015592

§ 371 (c)(1),
(2), (4) Date: Dec. 29, 2006

(87) PCT Pub. No.: WO2006/019195

PCT Pub. Date: Feb. 23, 2006

(65) Prior Publication Data

US 2008/0297725 A1    Dec. 4, 2008

(30) Foreign Application Priority Data

Aug. 20, 2004    (JP) .............................. 2004-241597

(51) Int. Cl.
*A61B 3/00* (2006.01)
(52) U.S. Cl. ........................................... 351/245
(58) Field of Classification Search ................ 351/245, 351/200, 205, 208, 209
See application file for complete search history.

(56) References Cited

U.S. PATENT DOCUMENTS 5,463,430 A    10/1995    Isogai et al.
5,903,336 A  *  5/1999    Kohayakawa ............... 351/245
6,120,149 A  *  9/2000    Hosoi ........................ 351/205

FOREIGN PATENT DOCUMENTS

| JP | U 04-58204    | 5/1992  |
|----|---------------|---------|
| JP | A 06-046999   | 2/1994  |
| JP | A 08-150115   | 6/1996  |
| JP | A 08-299274   | 11/1996 |
| JP | A 09-253048   | 9/1997  |
| JP | A 11-104080   | 4/1999  |
| JP | A 2001-046341 | 2/2001  |
| JP | A 2003-290144 | 10/2003 |
| JP | A 2004-129711 | 4/2004  |
| JP | A 2004-173724 | 6/2004  |

* cited by examiner

*Primary Examiner*—Ricky L Mack
*Assistant Examiner*—Tuyen Q Tra
(74) *Attorney, Agent, or Firm*—Oliff & Berridge, PLC

(57) ABSTRACT

To provide an ophthalmic apparatus by which an examiner can provide assistance such as lifting an examinee's eyelid while easily observing an observation image of an examinee's eye displayed on a monitor. The ophthalmic apparatus has a measurement part including a measurement optical system for examining or measuring the examinee's eye, a fixed support part which supports the measurement part to be movable, an observation optical system provided in the measurement part and having an image-pickup element, for observing an anterior segment of the eye, a monitor which displays an image of the anterior segment picked up by the element, and a holding unit which holds the monitor to be movable with respect to the measurement part or the fixed support part to change a placement position of the monitor between a first position where its screen is approximately vertical and a second position where the screen is approximately horizontal.

4 Claims, 5 Drawing Sheets

OPHTHALMIC APPARATUS

TECHNICAL FIELD

The present invention relates to an ophthalmic apparatus for examining or measuring an examinee's eye.

BACKGROUND ART

As an ophthalmic apparatus such as an eye refractive power measurement apparatus, a corneal shape measurement apparatus and a non-contact tonometer, generally known is a stationary-type apparatus which is used in a state where an examiner and an examinee sit facing each other with the apparatus placed between them. In this type of apparatus, a monitor for displaying an observation image and the like of an examinee's eye is fixedly placed at the examiner's side of the apparatus with its screen approximately vertical. Then, the examiner, being seated, operates the apparatus to perform examination or measurement while observing the observation image of the examinee's eye displayed on the monitor. However, when the examiner has to provide assistance such as lifting an eyelid of the examinee, the examiner has to assume an unnatural position in order to provide the assistance while observing the observation image of the examinee's eye displayed on the monitor, which is not easy.

The present invention has been made in view of the above circumstances and has an object to overcome the above problems and to provide an ophthalmic apparatus by which an examiner can provide assistance such as lifting an eyelid of an examinee while easily observing an observation image of an examinee's eye displayed on a monitor.

DISCLOSURE OF THE INVENTION

To solve the above problems, the present invention is characterized as having configurations described below.

An ophthalmic apparatus has a measurement part including a measurement optical system for examining or measuring an examinee's eye, a fixed support part which supports the measurement part to be movable, an observation optical system provided in the measurement part and having an image-pickup element, for observing an anterior segment of the examinee's eye, a monitor which displays an image of the anterior segment picked up by the image-pickup element, and a holding unit which holds the monitor to be movable with respect to the measurement part or the fixed support part so as to change a placement position of the monitor between a first position where a screen of the monitor is approximately vertical and a second position where the screen is approximately horizontal.

BEST MODE FOR CARRYING OUT THE INVENTION

Figure 1:
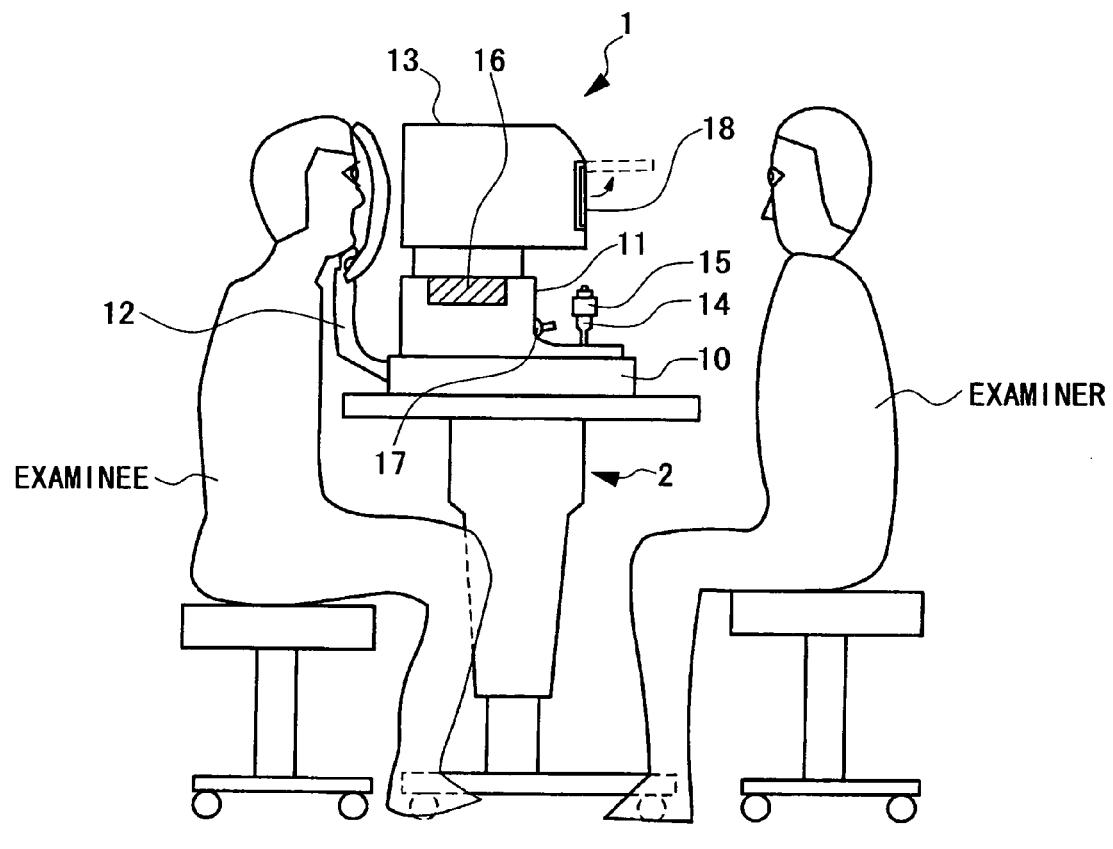
FIG. 1 is a view showing a schematic configuration of an ophthalmic apparatus consistent with the preferred embodiment of the present invention.

A detailed description of one preferred embodiment of the present invention is provided below with reference to the accompanying drawings. FIG. 1 is a view showing a schematic configuration of an ophthalmic apparatus consistent with the preferred embodiment of the present invention.

An ophthalmic apparatus 1 is a stationary-type apparatus used while being mounted on an electrically operated table 2. The apparatus 1 is used in a state where an examiner and an examinee sit on chairs facing each other with the apparatus 1 placed between them.

The apparatus 1 includes a base 10, a movable base 11 which is movable on the base 10 in a right-and-left direction and a back-and-forth direction by tilting operation of a joystick 14, a measurement part 13 which is movable on the movable base 11 in a three-dimensional direction of the right-and-left direction (hereinafter referred to as an X-direction), an up-and-down direction (hereinafter referred to as a Y-direction) and the back-and-forth direction (hereinafter referred to as a Z-direction) by a three-dimensional movement part 16, and a face supporting unit 12 which is fixed to the base 10 for supporting a face of the examinee. In the movement part 16, arranged are a Y table which is movable in the Y-direction, a Z table which is movable in the Z-direction and placed on the Y-table, and an X table which is movable in the X-direction and placed on the Z table. The measurement part 13 is placed on the X table and is moved in the three-dimensional direction by moving the Y table, the Z table and the X table using a motor or the like. A stopper mechanism 17 fixes the movable base 11 to the base 10.

On the examiner's side, which is the front side of the measurement part 13, provided is a monitor 18 (a liquid crystal display in this preferred embodiment) which displays an image of an anterior segment of an examinee's eye, which is an observation image thereof, a measurement result and the like. The monitor 18 is placed on the measurement part 13 in an approximately vertical position (a standard position), and is made so that its placement position can be changed/adjusted from the approximately vertical position to an approximately horizontal position.

Incidentally, the monitor 18 may also be provided either on the movable base 11 or on the base 10. In other words, the monitor 18 may be provided either on the movable part or on the fixed part of the apparatus 1.

Figure 2:
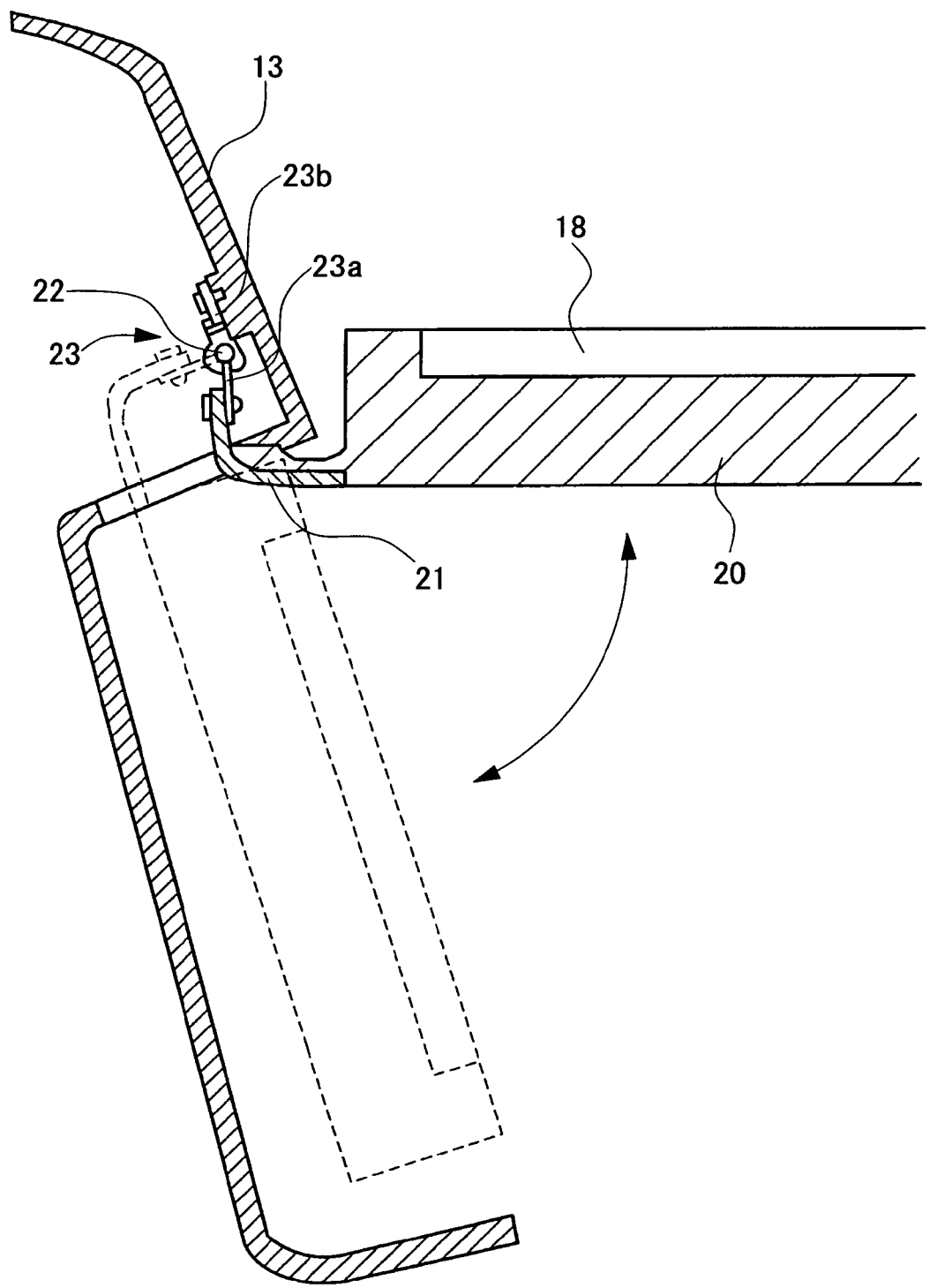
FIG. 2 is a view showing a schematic configuration of a mechanism for holding a monitor.
Figure 3:
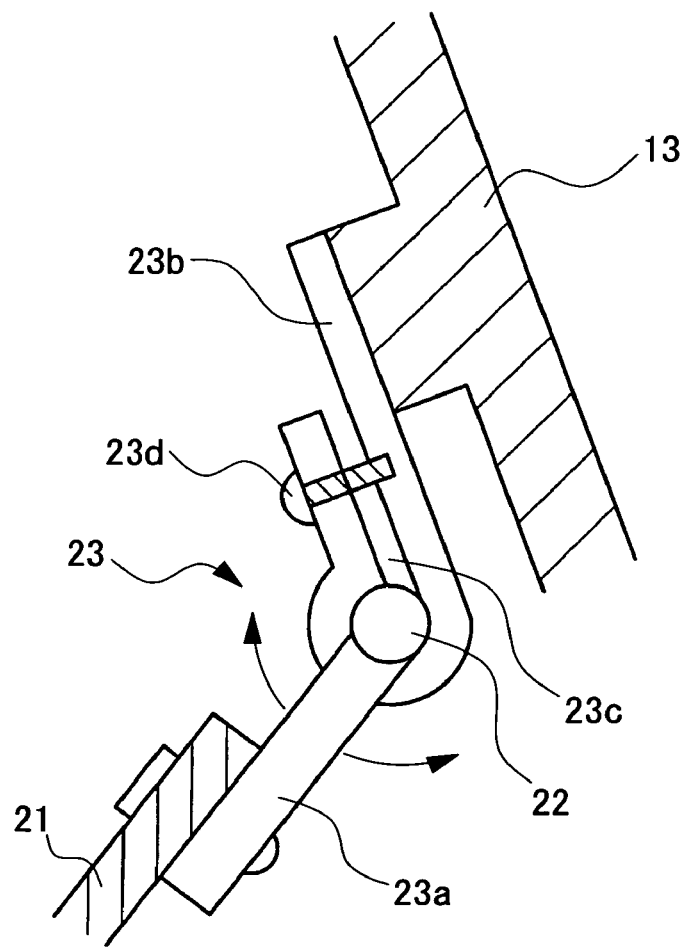
FIG. 3 is a view showing the schematic configuration of the mechanism for holding the monitor.

FIG. 2 and FIG. 3 are views showing a schematic configuration of a mechanism for holding the monitor 18. In the preferred embodiment, a free-stop hinge mechanism is used as the mechanism for holding the monitor 18. In other words, an L-shape metal fitting 21 is fixed to a frame 20 to which the monitor 18 is fixed. The metal fitting 21 is attached to a first arm 23a of a free-stop hinge 23. A shaft 22 of the first arm 23a passes through a hole of a second arm 23b of the free-stop hinge 23, the second arm 23b being fixed to a housing of the measurement part 13. Then, by adjusting a space of a clearance 23c of the second arm 23b while tightening a screw 23d, the shaft 22 is made to rotate when force is exerted thereon at a predetermined level or more while made fixed by friction when no force is exerted thereon. By such a mechanism, the placement position of the monitor 18 can be changed/adjusted from the approximately vertical position indicated with dotted lines to the approximately horizontal position indicated with solid lines in FIG. 2, and the placement position can be kept even in the approximately horizontal position or even in an inclined position between the approximately vertical position and the approximately horizontal position.

Incidentally, the monitor 18 may be kept horizontal by a click mechanism, a stopper mechanism or the like. In addition, the monitor 18 may be kept horizontal with a certain inclination (an angle of about 10 degrees) with respect to a horizontal direction because it is essential only for the examiner to see the screen easily, for example, when using the apparatus 1 while standing at the side thereof. In addition, the monitor 18 may be kept vertical with a certain inclination (an angle of about 15 degrees) with respect to a vertical direction because it is essential only for the examiner to see the screen easily, for example, when using the apparatus 1 while sitting in front thereof.

Figure 4:
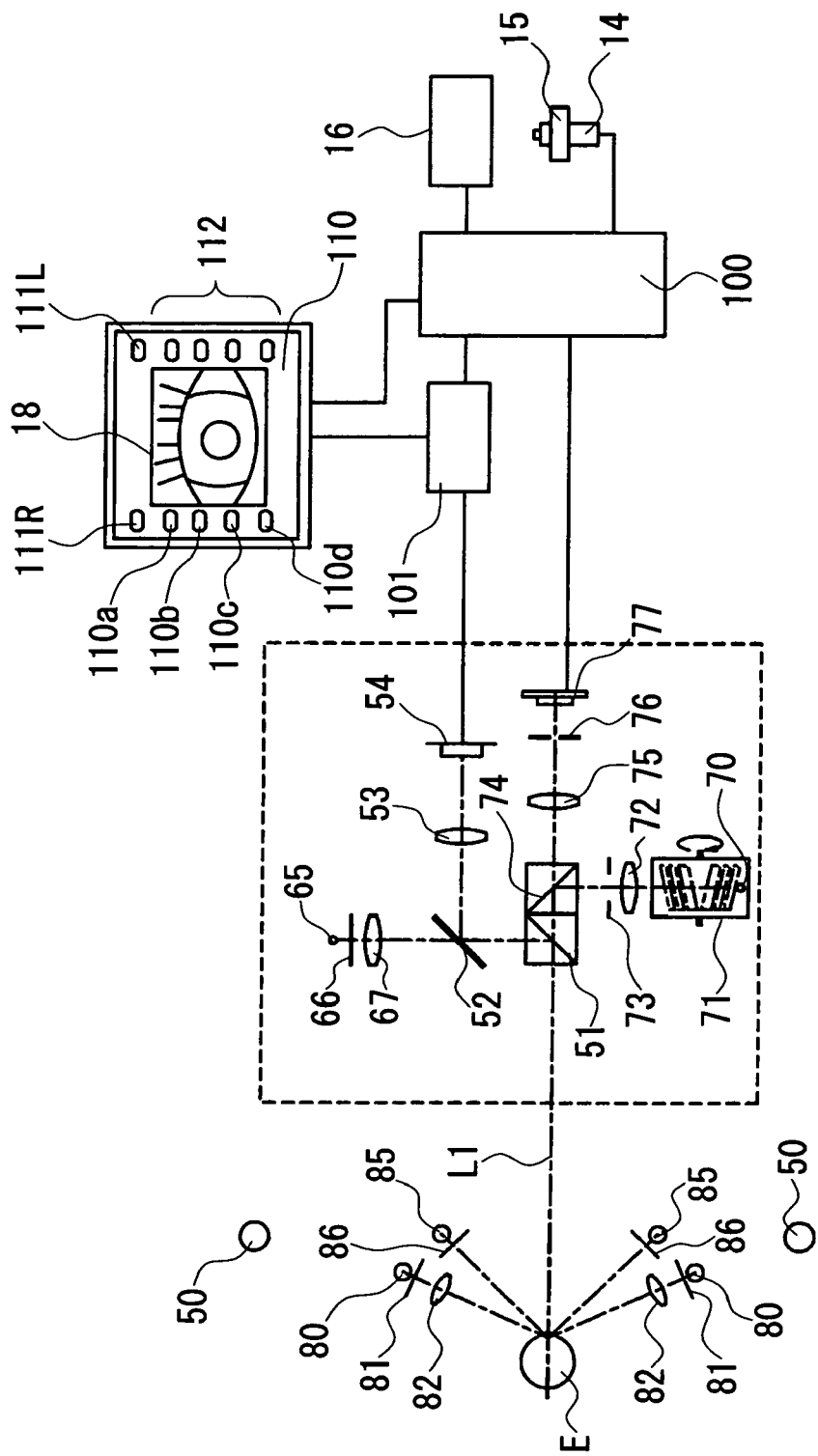
FIG. 4 is a view showing a schematic configuration of an optical system and a control system of the present apparatus.

FIG. 4 is a view showing a schematic configuration of an optical system housed in the measurement 13 and a control system of the apparatus 1.

An anterior-segment observation (image-pickup) optical system: an image of an anterior segment of an examinee's eye E by infrared light sources 50 for anterior-segment illumination is picked up by a CCD camera 54 being an image-pickup element via a half mirror 51, a half mirror 52 and an image forming lens 53. The anterior-segment image picked up by the CCD camera 54 is displayed on the monitor 18.

A fixation target presenting optical system: light through a fixation target 66 from a visible light source 65 for fixation target presentation heads for the eye E via a projection lens 67, the half mirror 52 and the half mirror 51. At the time of eye refractive power measurement, the projection lens 67 is moved in a direction of an optical axis L1 to fog the eye E.

An eye refractive power measurement optical system: measurement light from an infrared light source 70 for eye refractive power measurement is projected onto a fundus of the eye E while being scanned thereon via slits of a rotation sector 71, a projection lens 72, a diaphragm 73, a half mirror 74 and the half mirror 51. The measurement light reflected from the fundus is photo-received on a photo-receiving part 77 including a plurality of pairs of photo-receiving elements, via the half mirror 51, the half mirror 74, a photo-receiving lens 75 and a diaphragm 76. This eye refractive power measurement optical system adopts a phase-difference method as a measurement principle.

A corneal shape measurement optical system: measurement light from infrared light sources 80 for corneal shape measurement is projected onto a cornea of the eye E via spot openings 81 and collimating lenses 82. The measurement light reflected from the cornea is photo-received on the CCD camera 54 via the half mirror 51, the half mirror 52 and the image forming lens 53. Incidentally, the four light sources 80 are arranged having the optical axis L1 as their center, the optical axis L1 being a reference optical axis for eye refractive power measurement and corneal shape measurement. Two of the light sources 80 are arranged in a direction horizontal to the apparatus and the other two are arranged in a direction vertical to the apparatus so that projection optical axes in the horizontal direction and projection optical axes in the vertical direction respectively intersect at a predetermined angle with respect to the optical axis L1.

An alignment optical system: A corneal reflection image by the light source 70 is picked up by the CCD camera 54 via the half mirror 51, the half mirror 52 and the image forming lens 53, and used as an alignment target in the X-direction and the Y-direction. In addition, corneal reflection images by the light sources 80 arranged in the horizontal direction are picked up by the CCD camera 54 and used as alignment targets in the Z-direction. Alignment light by infrared light sources 85 for alignment in the Z-direction is projected onto the cornea of the eye E via spot openings 86. Corneal reflection images by the light sources 85 are picked up by the CCD camera 54 via the half mirror 51, the half mirror 52 and the image forming lens 53. Besides, the two light sources 85 are arranged having the optical axis L1 as their center, and they are arranged in the direction horizontal to the apparatus so that projection optical axes thereof intersect at a predetermined angle with respect to the optical axis L1.

Since the light from the light sources 80 is a parallel light bundle, positions of the corneal reflection images hardly change even if a working distance of the measurement part 13 (a distance in the Z-direction) with respect to the eye E varies. On the other hand, since the light from the light sources 85 is a divergent light bundle, positions of the corneal reflection images change if the working distance of the measurement part 13 varies. Accordingly, by comparing an interval between the corneal reflection images by the two light sources 80 and an interval between the corneal reflection images by the two light sources 85, an alignment state in the Z-direction of the measurement part 13 with respect to the eye E can be detected (see U.S. Pat. No. 5,463,430 corresponding to Japanese Patent Application Unexamined Publication No. Hei6-46999).

An output of the CCD camera 54 is connected to an image processing/display control part 101, and the control part 101 detects and processes the corneal reflection images for alignment and corneal shape measurement. In addition, the control part 101 controls the monitor 18 to display a screen. The control part 101, the photo-receiving part (photo-receiving element) 77, the movement part 16, a rotation knob 15 provided to the joystick 14, a switch part 110 arranged around the monitor 18, and the like are connected to a main calculation control part 100. The switch part 110 is provided with a plurality of switches by which predetermined signals are input, such as a switch 110a to make a changeover between measurement modes, a switch 110b to make a changeover between automatic alignment and manual alignment, a switch 110c for printing out the measurement result, a switch 110d for deleting data, a plurality of switches 112 for inputting signals according to the respective measurement modes, and two switches of a switch 111R and a switch 111L for making a changeover of a display direction of the anterior-segment image on the monitor 18 to a state where the display direction is rotated 90 degrees clockwise and to a state where the display direction is rotated 90 degrees counterclockwise. In addition, the control part 100 has a function of obtaining eye refractive power based on an output from the photo-receiving element 77, a function of obtaining a corneal shape based on the corneal reflection images detected by the control part 101, a function of detecting alignment states in the X-, Y-, and Z-directions of the measurement part 13 with respect to the eye E based on the corneal reflection images detected by the control part 101 to drive and control the movement part 16, and the like.

Next, operations by the apparatus 1 at the time of measurement will be described hereinafter. As shown in FIG. 1, the examinee is seated on the chair, and the examinee's face is fixed by the face supporting unit 12. The examiner usually sits on the chair to face the examinee with the apparatus 1 placed between them. In this case, the monitor 18 is brought to the approximately vertical state so that the examiner can see the screen easily while seated. The examiner, while observing the monitor 18, performs the tilting operation of the joystick 14 to move the movable base 11 in the X- and Z-directions so that the displayed anterior-segment image is positioned at the center of the screen, and performs rotating operation of the rotation knob 15 to move the measurement part 13 in the Y-direction. When the corneal reflection images by the light sources 70, 80 and 85 are picked up by the camera 54, and the control part 101 is brought to a state where the alignment state in the X-, Y-, and Z-directions can be detected, the automatic alignment and automatic tracking are to be started. The control part 100 drives and controls the movement part 16 based on the corneal reflection image by the light source 70 to move the measurement part 13 in the X- and Y-directions. In addition, the control part 100 drives and controls the movement part 16 based on the corneal reflection images by the light sources 80 and the light sources 85 arranged in the horizontal direction to move the measurement part 13 in the Z-direction. When the alignment in the X-, Y-, and Z-directions is completed, the control part 100 automatically transmits a trigger signal to perform the measurement. When a continuous measurement mode of continuously performing the corneal shape measurement and the eye refractive power measurement is selected, the measurement is performed continuously.

Figure 5:
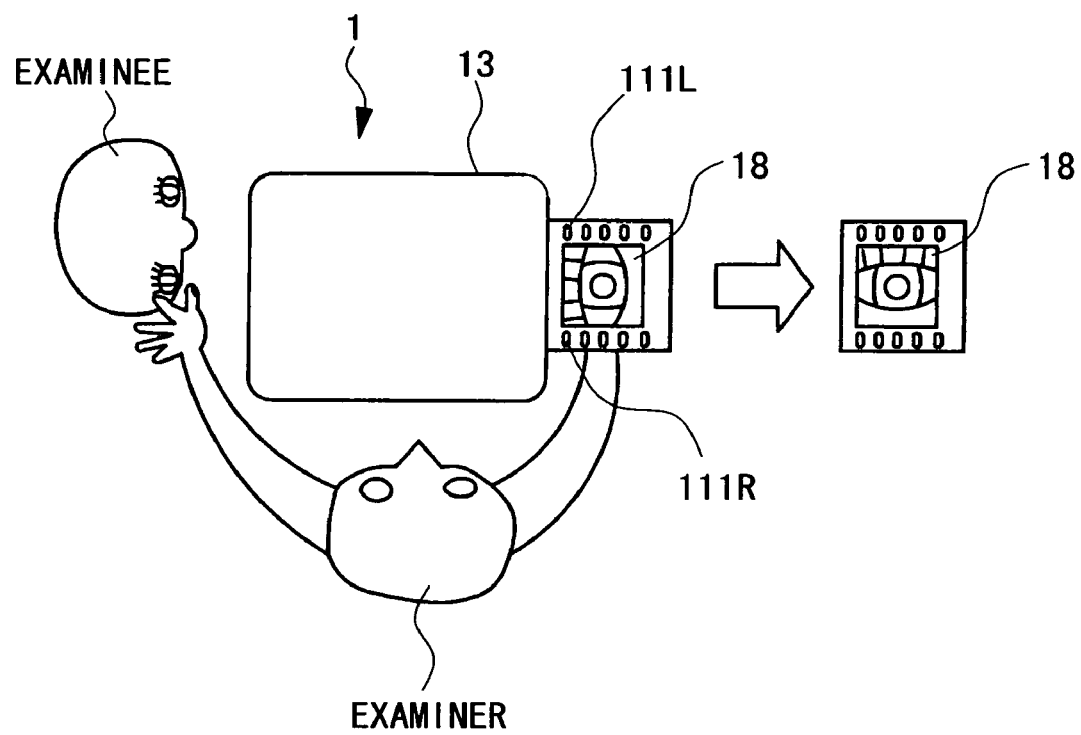
FIG. 5 is a view showing a state where an examiner performs measurement while standing at the side of the ophthalmic apparatus.

Here, if the examinee has a drooping eyelid (an eye not completely opened), the corneal reflection images cannot be detected, so that the automatic alignment cannot be performed, and neither can the subsequent measurement. Especially in the corneal shape measurement, the corneal reflection images cannot be detected, resulting in a measurement error. In such a case, the examiner, as shown in FIG. 5, stands at the side of the apparatus 1 and lifts the examinee's eyelid with one hand, and then lifts the frame 20 with the other hand to bring the monitor 18 to the approximately horizontal state. Accordingly, the examiner can easily observe the anterior-segment image displayed on the monitor 18 while standing at the side of the apparatus 1 and lifting the examinee's eyelid. In addition, the switch part 110 provided around the monitor 18 is also brought to the approximately horizontal state integrally with the monitor 18, so that the switch part 110 can be easily operated.

In addition, when the examiner presses either of the switch 111R or 111L, which is the one placed at the side where the examiner stands, the image processing/display control part 101 controls to rotate the display direction of the anterior-segment image on the monitor 18 90 degrees according to a direction indicated by the pressed switch. In other words, if the examiner performs the measurement while standing at the right side of the apparatus 1 as shown in FIG. 5, a changeover of the display direction of the anterior-segment image is made to the state rotated 90 degrees clockwise by pressing the switch 111R. Accordingly, states of the examinee's eye E, e.g., the extent to which the eyelid is open, the extent to which eyelashes cover the eye, and the extent to which a pupil is enlarged, are made easier to observe, allowing proper treatment to be performed. If the examiner performs the measurement while standing at the left side of the apparatus 1, a changeover of the display direction of the anterior-segment image is made to the state rotated 90 degrees counterclockwise by pressing the switch 111L. Besides, pressing the switch 111R or 111L again restores the display direction of the anterior-segment image.

Incidentally, while described in the above is the case where the examiner performs the measurement while standing at the side of the apparatus 1, also in a case where the examiner performs the measurement while standing to face the examinee, it is convenient for the monitor 18 to be made approximately horizontal, which is needless to say.

Various modifications may be applied to the above preferred embodiment. For example, as a method of rotating the display direction of the anterior-segment image 90 degrees clockwise or counterclockwise, the monitor 18 in itself may be rotated.

The invention claimed is:

1. An ophthalmic apparatus comprising:
    a base;
    a face supporting unit which is fixed to the base for supporting a face of an examinee;
    a measurement part which includes a measurement optical system for performing one of examination and measurement on an eye of the examinee with the face supported by the face supporting unit and that is movable on the base by operation of a joystick;
    an observation optical system provided in the measurement part and having an image-pickup element for observing the examinee's eye;
    a monitor which displays an image of the examinee's eye picked up by the image-pickup element;
    a frame to one side of which the monitor is fixed; and
    a holding unit which is mounted on the measurement part and holds the frame to be rotatably movable with respect to the measurement part,
    wherein the holding unit has a mechanism which holds the frame to be rotatably movable between a first position where the frame is approximately vertical for allowing the monitor to face an opposite direction to the face supporting unit, and a second position where the frame is approximately horizontal for allowing the monitor to face upward, and which holds the frame to be in a stationary state in at least one of the first position and the second position.

2. The ophthalmic apparatus according to claim 1, further comprising a changeover unit which makes a changeover of a display direction of the image on the monitor by rotating the display direction approximately 90 degrees clockwise or counterclockwise.

3. The ophthalmic apparatus according to claim 2, wherein the changeover unit includes a display control part which controls a screen of the monitor.

4. The ophthalmic apparatus according to claim 1, further comprising a switch part which is placed on the side of the frame on which the monitor is placed and includes a switch to be operated while the image on the monitor is observed.

* * * * *